US00PP24141P3

(12) United States Plant Patent
Zaiger et al.

(10) Patent No.: US PP24,141 P3
(45) Date of Patent: Jan. 7, 2014

(54) PEACH TREE NAMED 'SNOW BLISS'

(50) Latin Name: *Prunus persica*
Varietal Denomination: Snow Bliss

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 146 days.

(21) Appl. No.: 13/385,695

(22) Filed: Mar. 2, 2012

(65) Prior Publication Data

US 2013/0232649 P1 Sep. 5, 2013

(51) Int. Cl.
*A01H 5/00* (2006.01)

(52) U.S. Cl.
USPC ..... Plt./195

(58) Field of Classification Search
USPC ..... Plt./195
See application file for complete search history.

(56) References Cited

U.S. PATENT DOCUMENTS

| | | | | | |
|---|---|---|---|---|---|
| PP8,070 | P | * | 12/1992 | Zaiger et al. | Plt./196 |
| PP9,002 | P | * | 12/1994 | Zaiger et al. | Plt./197 |
| PP9,673 | P | * | 10/1996 | Zaiger et al. | Plt./197 |
| PP9,860 | P | * | 4/1997 | Zaiger et al. | Plt./197 |
| PP13,175 | P2 | * | 11/2002 | Howard | Plt./195 |
| PP17,911 | P3 | * | 8/2007 | Clark et al. | Plt./195 |
| PP22,606 | P3 | * | 3/2012 | Zaiger et al. | Plt./197 |

* cited by examiner

*Primary Examiner* — Wendy C Haas

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular production of large size fruit.
3. Fruit with a high degree of attractive red skin color.
4. Firm, white flesh fruit with very good flavor and eating quality.
5. Fruit with very good storage and shipping quality.

1 Drawing Sheet

Botanical designation: *Prunus persica.*
Variety denomination: 'Snow Bliss'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach trees, which are known to us, and mentioned herein, 'Zee Diamond' Peach (U.S. Plant Pat. No. 9,673), 'Earlirich' Peach (U.S. Plant Pat. No. 9,002), 'Summer Sweet' Peach (U.S. Plant Pat. No. 8,070), 'Super Rich' Peach (U.S. Plant Pat. No. 9,860) and our proprietary non-patented peach seedling selections '175LE263', '58ZA508' and '159LE553'.

ORIGIN OF THE VARIETY

The new and distinct variety of peach tree (*Prunus persica*) was developed by us in our experimental orchard located near Modesto, Calif. as a first generation cross between two proprietary peach seedlings with the field identification numbers '175LE263' (non-patented) and '58ZA508' (non-patented). The seed parent '175LE263' (non-patented) originated as a first generation cross between 'Zee Diamond' Peach (U.S. Plant Pat. No. 9,673) and 'Earlirich' Peach (U.S. Plant Pat. No. 9,002). The pollen parent '58ZA508' (non-patented) originated as a first generation cross between 'Super Rich' Peach (U.S. Plant Pat. No. 9,860) and our proprietary white flesh peach seedling '159LE553' (non-patented). A large group of these first generation seedlings were grown and maintained on their own root system and under close and careful observation we recognized the desirable fruit and tree characteristics of the present new variety and selected it in 2003 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a productive and regular bearer of large size, firm, white flesh, clingstone fruit with very good flavor and eating quality. The fruit is further characterized by having an attractive red skin color and good handling and storage quality. In comparison to its seed parent '175LE263' peach (non-patented) the fruit of the new variety has white flesh compared to yellow and ripens approximately 17 days later. In comparison to its pollen parent '58ZA508' peach (non-patented) the fruit of the new variety ripens approximately 7 days earlier. In comparison to the commercial variety 'Summer Sweet' Peach (U.S. Plant Pat. No. 8,070) the fruit of the new variety has a higher degree of red skin color, is clingstone instead of freestone and the fruit ripens approximately 7 days earlier.

PHOTOGRAPH OF THE VARIETY

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 8 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 8 year old specimens grown near Modesto, Calif., with color in accordance with Munsell Book of Color.

Tree:

*Size*.—Large, usually pruned to 3 to 3.5 meters in height and width for economical harvesting of fruit. Size varies with different cultural practices.

*Vigor*.—Vigorous, growth of 1.5 to 2.5 meters the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, normal fruit thinning necessary for desirable market size fruit. Fruit set varies with climatic conditions during blooming season.

*Bearer*.—Regular, adequate fruit set 5 consecutive years.

*Fertility*.—Self-fertile.

*Density*.—Medium dense, pruning to open center of tree to vase shape desirable to enhance fruit color and keep fruit wood healthy.

*Hardiness*.—Hardy in all stone fruit growing areas of California. Tree grown in USDA Hardiness Zone 9. Winter chilling requirement approximately 850 hours at or below 45° F.

Trunk:

*Size*.—Large, circumference of 45.7 cm at 30.5 cm above the ground on a 8 year old tree.

*Stocky*.—Medium stocky.

*Texture*.—Medium shaggy, roughness increases with age.

*Color*.—Varies from 10YR 3/4 to 2.5Y 4/2.

Branches:

*Size*.—Medium. Average circumference 16.4 cm at 1.2 meters above ground. Crotch angle approximately 35°, increases with heavy crop load.

*Surface texture*.—New growth relatively smooth. Mature growth medium rough, roughness increases with age.

*Lenticels*.—Average 23 in a 25.8 sq cm section. Average length 3.7 mm. Average width 2.0 mm. Color varies from 7. YR 6/8 to 7.5YR 5/8.

*Color*.—New growth 5GY 6/8 with 5R 3/8 where exposed to the sun. Old growth varies from 10YR 3/4 to 2.5Y 4/2, varies with age of growth.

Leaves:

*Size*.—Large. Average length 141.5 mm. Average width 41.0 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slightly indented over midrib and leaf veins. Lower surface relatively smooth except for small ridges created by midrib and pinnate venation. Both surfaces glabrous.

*Petiole*.—Average length 11.1 mm. Average width 1.6 mm. Surface — glabrous. Longitudinally grooved. Color — 5GY 5/8.

*Glands*.—Reniform. Size — medium to large. Average length 1.5 mm. Average diameter 0.8 mm. Number varies from 1 to 4, average number 2. Located primarily on the base of the leaf blade and the upper portion of the petiole. Color — 5GY 3/6.

*Stipules*.—None present.

*Color*.—Upper surface 7.5GY 3/2 to 10GY 3/2. Lower surface 10GY 3/4 to 2.5G3/2. Midvein color 5GY 5/2 to 7.5GY 5/2.

Flower buds:

*Size*.—Large. Average length 22.9 mm. Average diameter 14.7 mm.

*Hardiness*.—Hardy with respect to California winters.

*Form*.—Plump, conical, becoming elongated before opening.

*Pedicel*.—Average length 3.7 mm. Average width 1.3 mm. Color varies from 2.5GY 5/6 to 2.5GY 5/8.

*Color*.—Varies from 5RP 7/8 to 7.5RP 6/2.

Flowers:

*Blooming period*.—Date of First Bloom Mar. 5, 2011. Date of Petal Fall Mar. 13, 2011, varies slightly with climatic conditions.

*Size*.—Large, showy. Average height 22.1 mm. Average diameter 50.4 mm.

*Petals*.—Normally 5, alternately arranged to the sepals. Form — nearly globose, base narrows at point of attachment. Margin — sinuate. Average length 21.6 mm. Average width 19.5 mm. Color varies from 5RP 7/8 to 5RP 9/2, fades with age of flower.

*Sepals*.—Normally 5, alternately arranged to the petals. Shape — ovate, apex rounded. Margin — entire. Average length 7.0 mm. Average width 5.7 mm. Upper surface glabrous, lower surface pubescent. Color — upper surface varies from 2.5GY 5/8 to 5R 3/4. Lower surface varies from 7.5R 2/4 to 7.5R 2/6.

*Stamens*.—Average number per flower 42. Average filament length 16.4 mm. Filament color N 9.5/ (white) to 5RP 8/6 as flower ages. Anther color varies from 10R 4/10 to 10R 3/8.

*Pollen*.—Self-fertile. Color varies from 2.5Y 7/10 to 2.5Y 7/12.

*Pistil*.—Normally 1. Surface — pubescent. Average length 20.1 mm. Position of stigma even with anthers. Color varies from 10Y 8/6 to 2.5GY 8/6.

*Fragrance*.—Moderate.

*Color*.—Varies from 5RP 9/2 to 5RP 7/6.

*Number flowers per flower bud*.—One.

*Pedicel*.—Average length 4.4 mm. Average width 2.1 mm. Color varies from 2.5GY 6/8 to 5GY 6/6.

Fruit:

*Maturity when described*.—Firm ripe.

*Date of first picking*.—Jun. 27, 2011.

*Date of last picking*.—Jul. 5, 2011, varies slightly with climatic conditions.

*Size*.—Large. Average diameter axially 66.2 mm. Average transversely in suture plane 77.6 mm. Average weight 258.4 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Slightly retuse.

*Base*.—Flat to slightly retuse.

*Stem cavity*.—Rounded to slightly elongated in suture plane. Average depth 6.2 mm. Average diameter 8.6 mm.

Stem:

*Size*.—Small. Average length 10.0 mm. Average diameter 2.4 mm.

*Color*.—Varies from 2.5GY 6/6 to 2.5GY 5/6.

Flesh:

*Ripens*.—Relatively even.

*Texture*.—Firm, meaty, crisp.

*Fibers*.—Few, small, tender.

*Firmness*.—Good, holds firm on the tree for 6 to 7 days past maturity.

*Aroma*.—Moderate.

*Amydgalin*.—Undetected.

*Eating quality*.—Very good.

*Flavor*.—Very good, sweet, mild, low-acid flavor.

*Juice*.—Moderate amount, enhances flavor.

*Brix*.—Average Brix 14.0°, varies slightly with amount of fruit per tree and climatic conditions.

*Color*.—Varies from R-Y 8/5Y to 7.5Y 9/4.

*Size of pit cavity*.—Average length 42.0 mm. Average width 27.7 mm. Average depth 10.8 mm. Color varies from 5Y 9/4 to 5Y 8/4.

Skin:

*Thickness*.—Medium.

*Surface*.—Smooth.

*Pubescence*.—Present, moderate amount.

*Tendency to crack*.—None.

*Color*.—Ground color varies from 5Y 8.5/2 to 7.5Y 9/2. Overspread with 7.5R 3/8 to 7.5R 3/6.

*Tenacity*.—Tenacious to flesh.

*Astringency*.—None.

Stone:

*Type*.—Clingstone.

*Size*.—Large. Average length 37.2 mm. Average width 26.2 mm. Average thickness 20.5 mm.

*Form*.—Obovoid.

*Base*.—Flat.

*Apex*.—Pointed. Average length 1.2 mm.

*Surface*.—Pitted throughout, pits vary from rounded to slightly elongated.

*Sides*.—Unequal, with one side extending further from suture plane.

*Ridges*.—Numerous small ridges extending further from base to apex.

*Tendency to split*.—None.

*Color*.—Varies from 7.5YR 5/6 to 10R 3/8 when dry.

Kernel:

*Size*.—Medium to large. Average length 19.1 mm. Average width 11.7 mm. Average depth 6.3 mm.

*Form*.—Ovoid.

*Viability*.—Good, complete embryo development.

*Skin color*.—Varies from 5Y 9/4 to 7.5Y 9/4.

Use:

*Dessert*.—Market — local and long distance.

Keeping quality: Good, held firm in cold storage at 38° to 42° F. for 3 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. The new and distinct variety of peach tree (*Prunus persica*), substantially as illustrated and described.

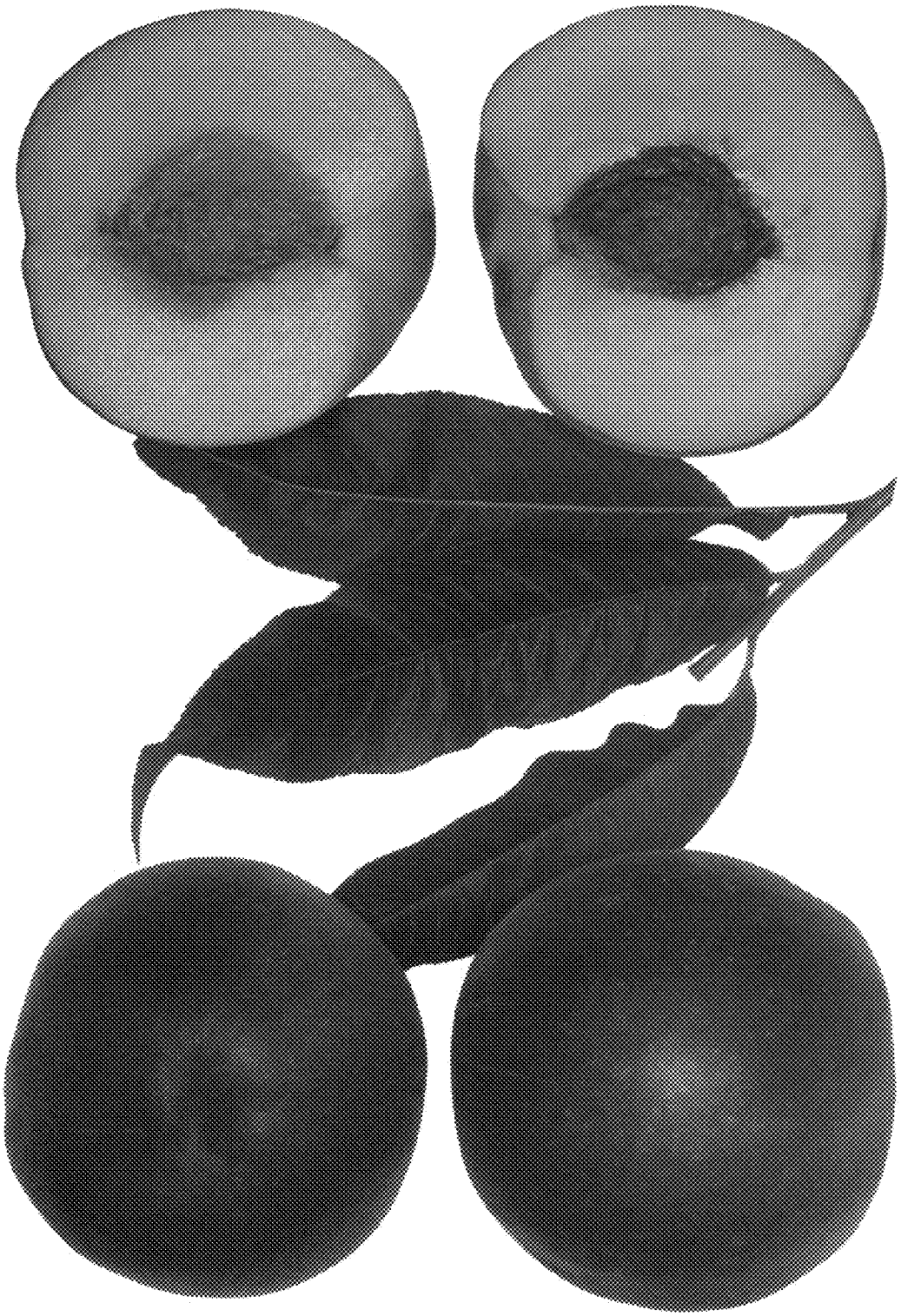

* * * * *